United States Patent
Schwartz et al.

(10) Patent No.: US 7,361,195 B2
(45) Date of Patent: Apr. 22, 2008

(54) CARTILAGE REPAIR APPARATUS AND METHOD

(75) Inventors: Herbert E. Schwartz, Ft. Wayne, IN (US); Prasanna Malaviya, Ft. Wayne, IN (US); Mark J. Pelo, Macy, IN (US); Pamela L. Plouhar, South Bend, IN (US)

(73) Assignee: DePuy Products, Inc., Warsaw, IN (US)

( * ) Notice: Subject to any disclaimer, the term of this patent is extended or adjusted under 35 U.S.C. 154(b) by 1122 days.

(21) Appl. No.: 10/195,347

(22) Filed: Jul. 15, 2002

(65) Prior Publication Data

US 2003/0036801 A1    Feb. 20, 2003

Related U.S. Application Data

(60) Provisional application No. 60/305,786, filed on Jul. 16, 2001, provisional application No. 60/389,027, filed on Jun. 14, 2002.

(51) Int. Cl.
*A61F 2/28* (2006.01)
(52) U.S. Cl. .................................... 623/23.63
(58) Field of Classification Search ............. 623/14.11, 623/14.12
See application file for complete search history.

(56) References Cited

U.S. PATENT DOCUMENTS

| 3,562,820 A | 2/1971 | Braun |
| 4,400,833 A | 8/1983 | Kurland |
| 4,642,120 A | 2/1987 | Nevo et al. |
| 4,873,976 A | 10/1989 | Schreiber |
| 4,880,429 A | 11/1989 | Stone |
| 4,902,508 A | 2/1990 | Badylak et al. |
| 4,919,667 A | 4/1990 | Richmond |
| 4,956,178 A | 9/1990 | Badylak et al. |
| 5,007,934 A | 4/1991 | Stone |
| 5,108,438 A | 4/1992 | Stone |
| 5,128,326 A | 7/1992 | Balazs et al. |
| 5,236,431 A | 8/1993 | Gogolewski et al. |
| 5,246,441 A | 9/1993 | Ross et al. |

(Continued)

FOREIGN PATENT DOCUMENTS

EP        0 446 105 A2    1/1992

(Continued)

OTHER PUBLICATIONS

Hodde et al., "The Effect of Range of Motion Upon Remodeling of Small Intestinal Submucosa (SIS) when used as an Achilles Tendon Repair Material in the Rabbit", *Tissue Engineering* 3, 1:27-37, (1997).

(Continued)

*Primary Examiner*—Corrine McDermott
*Assistant Examiner*—Christopher Prone
(74) *Attorney, Agent, or Firm*—Barnes & Thornburg LLP

(57) ABSTRACT

An orthopaedic device for repairing and regenerating cartilage includes a plug configured to be positioned in a hole formed in the cartilage and an anchor configured to support the plug. One or both of the plug and the anchor may be formed from naturally occurring extracellular matrix such as small intestine submucosa. A method for repairing and regenerating cartilage is also disclosed.

24 Claims, 6 Drawing Sheets

U.S. PATENT DOCUMENTS

| | | | |
|---|---|---|---|
| 5,275,826 A | 1/1994 | Badylak et al. |
| 5,281,422 A | 1/1994 | Badylak et al. |
| 5,306,311 A | 4/1994 | Stone et al. |
| 5,320,633 A | 6/1994 | Allen et al. |
| 5,352,463 A | 10/1994 | Badylak et al. |
| 5,372,821 A | 12/1994 | Badylak et al. |
| 5,374,268 A | 12/1994 | Sander |
| 5,380,334 A | 1/1995 | Torrie et al. |
| 5,445,833 A | 8/1995 | Badylak et al. |
| 5,460,962 A | 10/1995 | Kemp |
| 5,479,033 A | 12/1995 | Baca et al. |
| 5,516,533 A | 5/1996 | Badylak et al. |
| 5,554,389 A | 9/1996 | Badylak et al. |
| 5,569,252 A | 10/1996 | Justin et al. |
| 5,573,784 A | 11/1996 | Badylak et al. |
| 5,591,234 A | 1/1997 | Kirsch |
| 5,593,441 A | 1/1997 | Lichtenstein et al. |
| 5,601,558 A | 2/1997 | Torrie et al. |
| 5,632,745 A | 5/1997 | Schwartz |
| 5,641,518 A | 6/1997 | Badylak et al. |
| 5,645,860 A | 7/1997 | Knapp, Jr. et al. |
| 5,668,288 A | 9/1997 | Storey et al. |
| 5,669,912 A | 9/1997 | Spetzler |
| 5,677,355 A | 10/1997 | Shalaby et al. |
| 5,681,353 A | 10/1997 | Li et al. |
| 5,695,998 A | 12/1997 | Badylak et al. |
| 5,702,462 A | 12/1997 | Oberlander |
| 5,711,969 A | 1/1998 | Patel et al. |
| 5,730,933 A | 3/1998 | Peterson |
| 5,733,337 A | 3/1998 | Carr, Jr. et al. |
| 5,733,868 A | 3/1998 | Peterson et al. |
| 5,735,903 A | 4/1998 | Li et al. |
| 5,753,267 A | 5/1998 | Badylak et al. |
| 5,755,791 A | 5/1998 | Whitson et al. |
| 5,759,190 A | 6/1998 | Vibe-Hansen et al. |
| 5,759,205 A | 6/1998 | Valentini |
| 5,762,966 A | 6/1998 | Knapp et al. |
| 5,769,899 A | 6/1998 | Schwartz et al. |
| 5,788,625 A | 8/1998 | Plouhar et al. |
| 5,795,353 A | 8/1998 | Felt |
| 5,830,708 A | 11/1998 | Naughton |
| 5,842,477 A | 12/1998 | Naughton et al. |
| 5,847,012 A | 12/1998 | Shalaby et al. |
| 5,855,613 A | 1/1999 | Antanavich et al. |
| 5,855,619 A | 1/1999 | Caplan et al. |
| 5,866,414 A | 2/1999 | Badylak et al. |
| 5,885,265 A | 3/1999 | Patel et al. |
| 5,916,265 A | 6/1999 | Hu |
| 5,922,028 A | 7/1999 | Plouhar et al. |
| 5,954,723 A | 9/1999 | Spetzler |
| 5,954,747 A | 9/1999 | Clark |
| 5,955,110 A * | 9/1999 | Patel et al. .................. 424/551 |
| 5,958,874 A | 9/1999 | Clark et al. |
| 5,968,096 A | 10/1999 | Whitson et al. |
| 5,971,987 A | 10/1999 | Huxel et al. |
| 5,980,524 A | 11/1999 | Justin et al. |
| 5,981,825 A | 11/1999 | Brekke |
| 5,989,269 A | 11/1999 | Vibe-Hansen et al. |
| 5,993,475 A | 11/1999 | Lin et al. |
| 5,993,844 A | 11/1999 | Abraham et al. |
| 5,997,575 A | 12/1999 | Whitson et al. |
| 6,017,348 A | 1/2000 | Hart et al. |
| 6,027,744 A | 2/2000 | Vacanti et al. |
| 6,042,610 A | 3/2000 | Li et al. |
| 6,051,750 A | 4/2000 | Bell |
| 6,056,752 A | 5/2000 | Roger |
| 6,056,777 A | 5/2000 | McDowell |
| 6,056,778 A | 5/2000 | Grafton et al. |
| 6,060,640 A | 5/2000 | Pauley et al. |
| 6,068,648 A | 5/2000 | Cole et al. |
| 6,080,194 A | 6/2000 | Pachence et al. |
| 6,093,201 A | 7/2000 | Cooper et al. |
| 6,096,347 A | 8/2000 | Jaeger et al. |
| 6,099,567 A | 8/2000 | Badylak et al. |
| 6,126,686 A | 10/2000 | Badylak et al. |
| 6,146,385 A | 11/2000 | Torrie et al. |
| 6,152,935 A | 11/2000 | Kammerer et al. |
| 6,153,292 A | 11/2000 | Bell et al. |
| 6,156,044 A | 12/2000 | Kammerer et al. |
| 6,171,344 B1 | 1/2001 | Atala |
| 6,176,880 B1 | 1/2001 | Plouhar et al. |
| 6,179,840 B1 | 1/2001 | Bowman |
| 6,179,872 B1 | 1/2001 | Bell et al. |
| 6,187,039 B1 | 2/2001 | Hiles et al. |
| 6,206,931 B1 * | 3/2001 | Cook et al. .............. 623/23.75 |
| 6,214,049 B1 | 4/2001 | Gayer et al. |
| 6,224,892 B1 | 5/2001 | Searle |
| 6,235,057 B1 | 5/2001 | Roger et al. |
| 6,242,247 B1 | 6/2001 | Rieser et al. |
| 6,251,143 B1 * | 6/2001 | Schwartz et al. ........ 623/23.72 |
| 6,251,876 B1 | 6/2001 | Bellini et al. |
| 6,273,893 B1 | 8/2001 | McAllen, III et al. |
| 6,283,980 B1 | 9/2001 | Vibe-Hansen et al. |
| 6,288,043 B1 | 9/2001 | Spiro et al. |
| 6,293,961 B2 | 9/2001 | Schwartz et al. |
| 6,306,156 B1 | 10/2001 | Clark |
| 6,306,159 B1 | 10/2001 | Schwartz et al. |
| 6,306,177 B1 | 10/2001 | Felt et al. |
| 6,319,258 B1 | 11/2001 | McAllen, III et al. |
| 6,319,271 B1 | 11/2001 | Schwartz et al. |
| 6,326,025 B1 | 12/2001 | Sigler et al. |
| 6,333,029 B1 | 12/2001 | Vyakarnam et al. |
| 6,334,872 B1 | 1/2002 | Termin et al. |
| 6,355,699 B1 | 3/2002 | Vyakarnam et al. |
| 6,364,884 B1 | 4/2002 | Bowman et al. |
| 6,371,958 B1 | 4/2002 | Overaker |
| 6,379,367 B1 | 4/2002 | Vibe-Hansen et al. |
| 6,379,710 B1 | 4/2002 | Badylak |
| 6,383,221 B1 | 5/2002 | Scarborough et al. |
| 6,409,764 B1 | 6/2002 | White et al. |
| 2002/0019649 A1 | 2/2002 | Sikora et al. |
| 2002/0048595 A1 | 4/2002 | Geistlich |
| 2002/0099448 A1 | 7/2002 | Hiles |
| 2002/0173806 A1 | 11/2002 | Giannetti et al. |

FOREIGN PATENT DOCUMENTS

| | | |
|---|---|---|
| EP | 0 734 736 A1 | 10/1996 |
| JP | 11319068 A | 11/1999 |
| WO | WO 90/09769 | 9/1990 |
| WO | WO 94/11008 | 5/1994 |
| WO | WO 95/05083 | 2/1995 |
| WO | WO 95/22301 | 8/1995 |
| WO | WO 95/06439 | 9/1995 |
| WO | WO 95/32623 | 12/1995 |
| WO | WO 96/24661 | 8/1996 |
| WO | WO 97/37613 | 10/1997 |
| WO | WO 98/06445 | 2/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 99/03979 | 1/1999 |
| WO | WO 99/43786 | 9/1999 |
| WO | WO 99/47188 | 9/1999 |
| WO | WO 00/16822 | 3/2000 |
| WO | WO 00/24437 A2 | 5/2000 |
| WO | WO 00/24437 A3 | 5/2000 |
| WO | WO 00/32250 | 6/2000 |
| WO | WO 00/48550 | 8/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |

| WO | WO 01/45765 | 6/2001 |
| WO | WO 01/66159 | 9/2001 |

OTHER PUBLICATIONS

Ferrand et al., "Directional Porosity of Porcine Small-Intestinal Submucosa", *J Biomed Materials Res*, 27:1235-1241, (1993).
Hiles et al., "Porosity of Porcine Small-Intestinal Submucosa for use as a Vascular Graft", *J Biomed Materials Res*, 27: 139-144, (1993).
Hodde et al., "Glycosaminoglycan Content of Small Intestinal Submucosa: A Bioscaffold for Tissue Replacement", *Tissue Engineering*, 2:3, 209-217, (1996).
Prevel et al., "Small Intestinal Submucosa: Utilization for Repair of Rodent Abdominal Wall Defects", *Ann Plast Surg*, 35:374-380, (1995).
Clarke et al., "Intestine Submucosa and Polypropylene Mesh for Abdominal Wall Repair in Dogs", *J Surg Res*, 60:107-114, (1996).
Prevel et al., "Small Intestinal Submucosa: Utilization as a Wound Dressing in Full-Thickness Rodent Wounds", *Ann Plast Surg*, 35:381-388, (1995).
Cobb et al., "Histology after Dural Grafting with Small Intestinal Submucosa", *Surgical Neurology*, 46: 389-394, (1996).
Cobb et al., "Porcine Small Intestinal Submucosa as a Dural Substitute", *Surgical Neurology*, 51:99-104, (1999).
Voytik-Harbin et al., "Application and Evaluation of the AlamarBlue Assay for Cell Growth and Survival of Fibroblasts", *Journal of Immunological Methods, In Vitro Cell Bio-Animal*, 34: 2399-246, (1998).
Hiles et al., "Mechanical properties of xenogeneic small-intestinal submucosa when used as an aortic graft in the dog", *Journal of Biomedical Materials Research*, vol. 29, 883-891, (1995).
Sandusky, et al., "Healing Comparison of Small Intestine Submucosa and ePTFE Grafts in the Canine Carotid Artery", *J. Surg.Res.*, 58:415-420, (1995).
Knapp, et al., "Biocompatibility of Small-Intestine Submucosa in Urinary Tract as Augmentation Cystoplasty Graft and Injectable Suspension", *J Endourology*, 8:125-130, (1994).
Kropp et al., "Regenerative Bladder Augmentation: A Review of the Initial Preclinical Studies with Porcine Small Intestinal Submucosa", *Muscle, Matrix, and Bladder Function*, Plenum Press, New York, (1995).
Kropp et al., "Experimental Assessment of Small Intestinal Submucosa as a Bladder Wall Substitute", *Urology* 446:396-400, (1995).
Vaught et al., "Detrusor Regeneration in the Rat Using Porcine Small Intestinal Submucosa Grafts: Functional Innervation and Receptor Expression", *J. Urol.*, 155:374-378, (1996).
Kropp et al, Characterization of Small Intestinal Submucosa Regenerated Canine Detrusor: Assessment of Reinnervation, In Vitro Compliance and contractility, *J. of Urol*. 156:599-607, (1996).
Kropp et al., "Regenerative Urinary Bladder Augmentation Using Small Intestinal Submucosa: Urodynamic and Histopathologic Assessment in Long-Term Canine Bladder Augmentations", *Journal of Urology*, 155:2098-2104, (1996).
Aiken et al., "Small Intestinal Submucosa as an Intra-Articular Ligamentous Graft Material: A Pilot Study in Dogs", *Vet Comp Orthopedics Traumatology*, 7:124-128, (1994).
Badylak et al., "The Use of Xenogeneic Small Intestinal Submucosa as a Biomaterial for Achille's Tendon Repair in a dog model", *J Biomed Materials*, 29:977-985, (1995).
Suckow, M.A., "Enhanced Bone Regeneration Using Porcine Small Intestinal Submucosa", *J. Invest Surg*, 12: 277, (1999).
Badylak , S., et al., "Naturally Occurring Extracellular Matrix as a Scaffold for Musculoskeletal Repair", *Clin Orthop*, 3675:S333-S3433, (1999).
Cook, J.L. et al., "Induction of Meniscal Regeneration in Dogs Using a Novel Biomaterial", *Am J Sports Med*, 27: 658, (1999).
Dejardin, L.M. et al., "Use of small intestinal submucosal implants for regeneration of large fascial defects: an experimental study in dogs", *J Biomed Mater Res*, 46:203-211, (1999).

Sacks, M.S., et al., "Quantification of the fiber architecture and biaxial mechanical behavior of porcine intestinal submucosa", *J Biomed Mater Res*, 46:1-10, (1999).
COOK® News Releases, "COOK® Introduces Innovative Surgisis™ Soft Tissue Repair Biomaterial", (May 21, 2000).
COOK® News Releases, "COOK® Oasis™ Wound Dressing Biomaterial From COOK® Remodels Partial Thickness Skin Injuries", (Dec. 23, 1999).
COOK® News Releases, "Cook Incorporated Forms Dedicated Tissue Engineered Products Group", (Feb. 16, 2000).
COOK® News Releases, "FDA Clears Oasis™ Wound Dressing Biomaterial From COOK® For Full-Thickness Skin Injuries", (Jan. 24, 2000).
Klootwyk, et al., "The Use of Xenographic SIS as a Biomaterial for Achilles Tendon Repair in Dogs," First SIS Symposium, Dec. 1996, USA.
Lenz, et al., "SIS as an ACL Replacement in Dogs and Goats," First Symposium, Dec. 1996, USA.
Cook, et al., "Comparison of SIS Cancellous Bone as Substrates for Three-Dimensional Culture of Canine Articular Chondrocytes," First SIS Symposium, Dec. 1996, USA.
Badylak, et al., "Different Configurations of Small Intestinal Submucosa as a Biomaterial for Achilles Tendon Repair in a Dog Model," First SIS Symposium, Dec. 1996, USA.
Voytik-Harbin & Badylak, "Induction of Osteogenic Activity By Small Intestinal Submucosa in Rat Calvaria Non-union Defects," First SIS Symposium, Dec. 1996, USA.
Kandel, et al., "SIS and Reconstituted Cartilage and Its Use in Joint Resurfacing of Focal Defects in Rabbits," First SIS Symposium, Dec. 1996, USA.
Tullius, et al., "Differential Permeabilty of SIS," First SIS Symposium, Dec. 1996, USA.
Obermiller, et al., "Suture Retention Strength of SIS," First SIS Symposium, Dec. 1996, USA.
Shelton, et al., "Repair of the Canine Medial Meniscus using SIS: A Feasibility Study," Second SIS Symposium, Dec. 1998, USA.
Cook, et al., "Meniscal Regeneration in dogs Using Grafts of SIS," Second SIS Symposium, Dec. 1998, USA.
Welch, et al., "Healing of Canine Meniscal Defect with Small Intestinal Submucosa Implants," Dec. 1998, USA.
Solchaga, et al., "SIS as Delivery Vehicle for Mesenchymal Progenitor Cells," Dec. 1998, USA.
Paulino, et al., "The Use of an SIS-PGA Composite Graft for Repair of Cartilage Defect," Dec. 1998, USA.
Toombs and May, "Clinical Follow-Up of Three Canine ACL Reconstructions Using an SIS ACL Device," Dec. 1998, USA.
Tomasek and Gifford, "Small Intestinal Submucosa Matrix Regulates The Differentiation of Myofibroblasts," Third SIS Symposium, Nov. 2000, USA.
Cook, et al., "Tissue Engineering For Meniscal Repair Using SIS," Third SIS Symposium, Nov. 2000, USA.
Lifrak, et al., "Enhanced Repair of Goat Meniscal Defects Using Porcine Small Intestinal Submucosa (SIS)," Third SIS Symposium, Nov. 2000, USA.
Hoffman, "SIS Disc Replacement For the Temporomandibular Joint," Third SIS Symposium, Nov. 2000, USA.
Kaeding, "Use of SIS In The Surgical Treatment of Chronic Symptomatic Patella Tendinosis," Third SIS Symposium, Nov. 2000, USA.
Tomczak and Kaeding, "Use of SIS in The Surgical Treatment of Tendinosis About The Foot And Ankle," Third SIS Symposium, Nov. 2000, USA.
Moore, et al., "Bridging Segmental Defects In Long Bones With Intramedullary Tubes And Periosteal Sleeves Made From Small Intestinal Submucosa (SIS)," Third SIS Symposium, Nov. 2000, USA.
Wang, et al., "Small Intestinal Submucosa Enhances Healing of Medical Collateral Ligament In A Rabbit Model," Third SIS Symposium, Nov. 2000, USA.
Ojha, et al., "PGA-Plla Versus Small Intestinal Submucosa (SIS): A Comparison of Neo-Cartilage Grown From Two Scaffold Materials," Third SIS Symposium, Nov. 2000, USA.

Wiklerson, "Use of The Porcine Small Intestine Submucosal Tissue Graft And Repair of Rotator Cuff Tears," Third SIS Symposium, Nov. 2000, USA.

"Small Intestinal Submucosa," Third SIS Symposium, Nov. 2000, USA.

"Current Clinical Applications of SIS," Third SIS Symposium, Nov. 2000, USA.

Hodde, et al., "Glycosaminoglycan Content of Small Intestinal Submucosa: A Potential for GAG-Growth Interactions in SIS-Mediated Healing", First Symposium, Dec. 1996, USA.

* cited by examiner

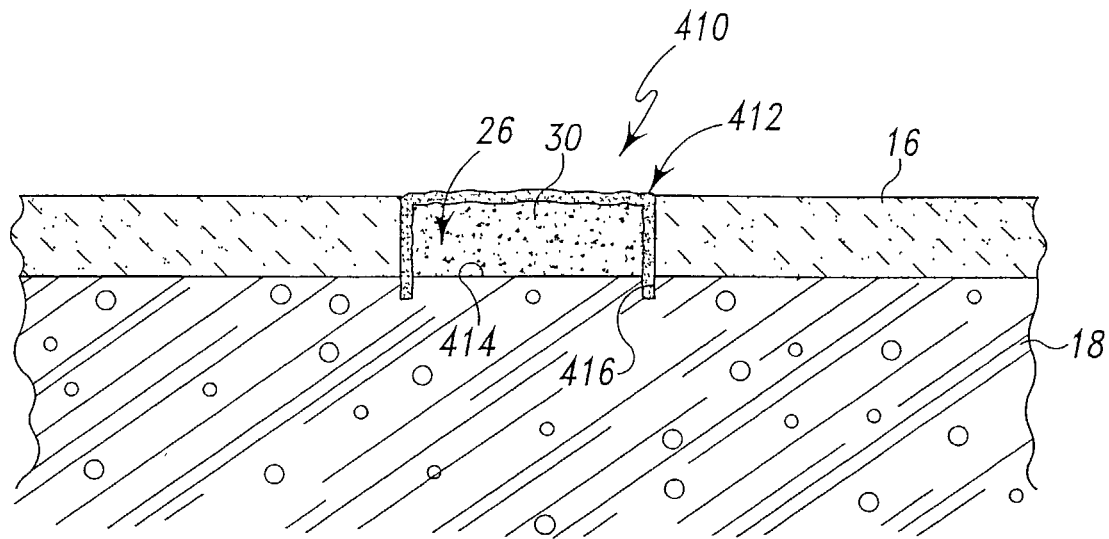
Fig. 5
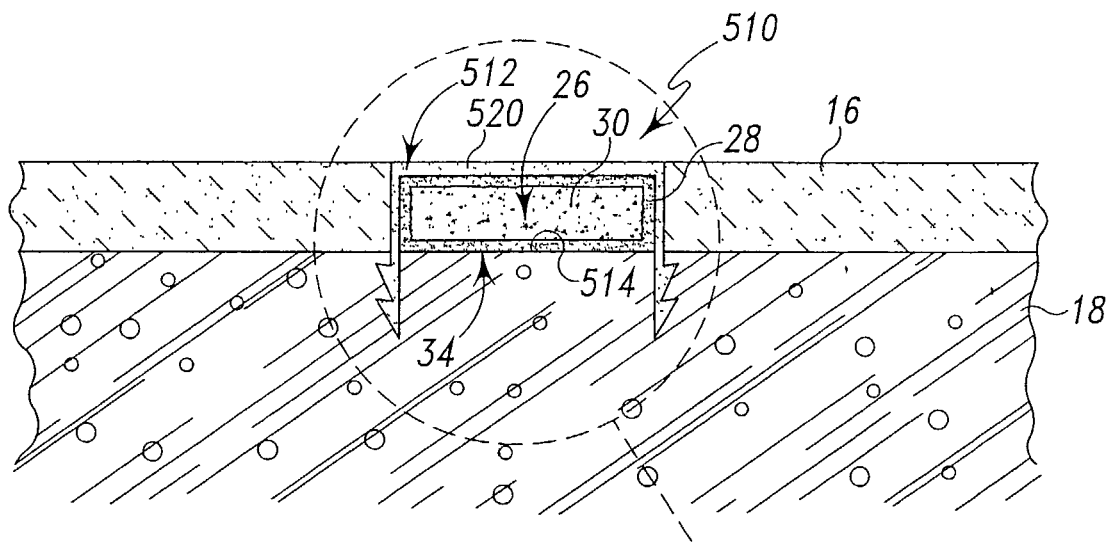
Fig. 6
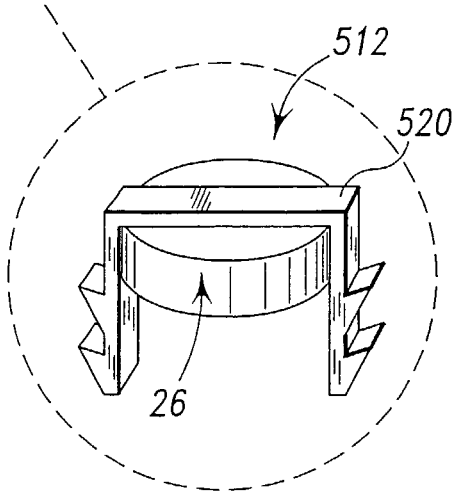

CARTILAGE REPAIR APPARATUS AND METHOD

This application claims priority under 35 U.S.C. § 119(e) to U.S. Provisional Application No. 60/305,786, filed Jul. 16, 2001; and U.S. Provisional Application No. 60/389,027, filed Jun. 14, 2002, both of which are expressly incorporated by reference herein.

CROSS REFERENCE

Cross reference is made to U.S. patent applications Ser. No. 10/195,795 entitled "Meniscus Regeneration Device and Method"; Ser. No. 10/195,719 entitled "Devices from Naturally Occurring Biologically Derived Materials"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; and Ser. No.10/195,633 entitled "Porous Delivery Scaffold and Method", each of which is assigned to the same assignee as the present application, each of which is filed concurrently herewith, and each of which is hereby incorporated by reference. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is hereby incorporated by reference.

FIELD OF THE DISCLOSURE

The present disclosure relates generally to devices for attaching, repairing, or regenerating damaged or diseased cartilage.

BACKGROUND

Articular cartilage is a type of hyaline cartilage that lines the surfaces of the opposing bones in a diarthrodial joint (e.g. knee, hip, shoulder, etc.). Articular cartilage provides a near-frictionless articulation between the bones, while also functioning to absorb and transmit the compressive and shear forces encountered in the joint. Further, since the tissue associated with articular cartilage is aneural, these load absorbing and transmitting functions occur in a painless fashion in a healthy joint.

However, when articular cartilage tissue is no longer healthy it can cause debilitating pain in the joint. Cartilage health can be affected by disease, aging, or trauma, all of which primarily involve a breakdown of the matrix consisting of a dense network of proteoglycan aggregates, collagen type 11 fibers, and other smaller matrix proteins. Cartilage cells, called chondrocytes, are unable to induce an adequate healing response because they are unable to migrate, being enclosed in lacunae surrounded by a dense matrix. Further, since the tissue is avascular, initiation of healing by circulating cells is not possible.

Several cartilage repair strategies have been attempted in the past. These include surgical techniques such as microfracturing or performing an abrasion arthroplasty on the bone bed to gain vascular access, and hence, stimulate extrinsic repair in the defective region.

Another surgical technique is mosaicplasty or osteochondral autograft transfer system (OATS). In this case, cylindrical plugs of healthy cartilage from a low-load bearing region of the knee are taken and transplanted into the defective region.

The only FDA-approved cartilage treatment in the market involves autologous chondrocyte implantation (CartiCel™). Autologous chondrocyte implantation involves performing an initial biopsy of healthy cartilage from the patient, isolating the cells from the tissue, expanding the cells in vitro by passaging them in culture, and then reintroducing them into the defective area. The cells are retained within the defect by applying a periosteal tissue patch over the defect, suturing the edges of the patch to the host tissue, and then sealing with fibrin glue. The healing observed is similar to that observed with microfracture or abrasion of the bone bed, indicating that it is the preparation of the bone bed and not the introduction of the cells that facilitates the healing process.

Tissue engineering strategies for healing cartilage are being investigated by several academic and commercial teams and show some promise. The approach primarily involves using a carrier or a scaffold to deliver cells or stimulants to the defect site. The scaffold material can be a purified biologic polymer in the form of a porous scaffold or a gel (purified collagens, glycoproteins, proteoglycans, polysaccharides, or the like in various combinations) or porous scaffolds of synthetic biodegradable polymers (PLA, PGA, PDS, PCL, or the like in various combinations). Several challenges remain with this approach, however. Some of these challenges include retention of the active stimulant at the defect site, inability to control the rate of release of the stimulant (resulting in tissue necrosis due to overdose), cytotoxicity of the cells due to the degradation by-products of the synthetic polymers.

As alluded to above, it is known to use various collagen scaffolds to provide a scaffold for repair and regeneration of damaged tissue. U.S. Pat. No. 6,042,610 to ReGen Biologics, hereby incorporated by reference, discloses the use of a device comprising a bioabsorbable material made at least in part from purified natural fibers. The purified natural fibers are crosslinked to form the device. The device can be used to provide augmentation for a damaged meniscus. Related patents U.S. Pat. Nos. 5,735,903, 5,479,033, 5,306,311, 5,007,934, and 4,880,429 also disclose a meniscal augmentation device for establishing a scaffold adapted for ingrowth of meniscal fibrochondrocyts.

It is also known to seed collagenous scaffolds with cells. See, e.g., U.S. Pat. Nos. 6,379,367 and 6,283,980, the disclosure of each of which is hereby incorporated by reference.

It is also known to use naturally occurring extracelluar matrices (ECMs) to provide a scaffold for tissue repair and regeneration. One such ECM is small intestine submucosa (SIS). SIS has been used to repair, support, and stabilize a wide variety of anatomical defects and traumatic injuries. Commercially available SIS material is derived from porcine small intestinal submucosa that remodels to the qualities of its host when implanted in human soft tissues. Further, it is taught that the SIS material provides a natural scaffold-like matrix with a three-dimensional microstructure and biochemical composition that facilitates host cell proliferation and supports tissue remodeling. Indeed, SIS has been shown to contain biological molecules, such as growth factors and glycosaminoglycans, that aid in the repair of soft tissue in the human body. SIS products, such as OASIS and SURGISIS, are commercially available from Cook Biotech Inc., of Bloomington, Ind.

Another SIS product, RESTORE® Orthobiologic Implant, is available from DePuy Orthopaedics, Inc. in Warsaw, Ind. The DePuy product is described for use during rotator cuff surgery, and is provided as a resorbable framework that allows the rotator cuff tendon to regenerate. The RESTORE Implant is derived from porcine small intestine submucosa, a naturally occurring ECM (composed of mostly collagen type I (about 90% of dry weight), glycosaminoglycans and other biological molecules) that has been cleaned, disinfected, and sterilized. During seven years of preclinical testing in animals, there were no incidences of infection transmission from the implant to the host, and the SIS material has not adversely affected the systemic activity of the immune system.

While small intestine submucosa is readily available, other sources of ECM are known to be effective for tissue remodeling. These sources include, but are not limited to, stomach, bladder, alimentary, respiratory, and genital submucosa, or liver basement membrane. See, e.g., U.S. Pat. Nos. 6,379,710, 6,171,344, 6,099,567, and 5,554,389, each of which hereby incorporated by reference.

For the purposes of this disclosure, it is within the definition of a naturally occurring ECM to clean and/or comminute the ECM, or to cross-link the collagen within the ECM. However, it is not within the definition of a naturally occurring ECM to separate and purify the natural fibers and reform a matrix material from purified natural fibers. Also, while reference is made to SIS, it is understood that other naturally occurring ECMs, such as stomach, bladder, alimentary, respiratory, or genital submucosa, or liver basement membrane, for example, whatever the source (e.g. bovine, porcine, ovine, etc.) are within the scope of this disclosure. Thus, as used herein, the terms "naturally occurring extracellular matrix" or "naturally occurring ECM" are intended to refer to extracellular matrix material that has been cleaned, disinfected, sterilized, and optionally cross-linked. The terms "naturally occurring extracellular matrix" and "naturally occurring ECM" are also intended to include ECM foam material prepared as described in copending U.S. patent application Ser. No. 10/195,354 entitled "Porous Extracellular Matrix Scaffold and Method", filed concurrently herewith.

The following patents, hereby incorporated by reference, disclose the use of ECMs for the regeneration and repair of various tissues: U.S. Pat. Nos. 6,379,710; 6,187,039; 6,176,880; 6,126,686; 6,099,567; 6,096,347; 5,997,575; 5,993,844; 5,968,096; 5,955,110; 5,922,028; 5,885,619; 5,788,625; 5,733,337; 5,762,966; 5,755,791; 5,753,267; 5,711,969; 5,645,860; 5,641,518; 5,554,389; 5,516,533; 5,460,962; 5,445,833; 5,372,821; 5,352,463; 5,281,422; and 5,275,826.

It is known to use such materials as catgut and SIS to make appliances. See the Bolesky published application WO 95/06439. The Bolesky application discloses devices that are semi-rigid and are formed into desired shapes, but Bolesky does not disclose a process for fabricating naturally occurring extracellular matrix parts so that they are rigid and hardened.

SUMMARY

The concepts of the present disclosure provide for an implantable, biodegradable cartilage repair device. In an illustrative embodiment, there is provided an implantable cartilage repair device which includes a plug formed of a naturally occurring extracellular matrix. The density and porosity of the extracellular matrix material can be controlled with compression drying, including air drying, air drying with heat, vacuum drying, vacuum drying with heat, and freeze drying. Thus, the ECM material can be dried to have a hardness sufficient to machine the device, without the need to form the device into the general shape by molding. By managing density and porosity of the ECM various matrices and fixation devices may be fabricated having superior material properties which allow the device to promote healing while remaining biodegradable.

In a more specific illustrative embodiment, there is provided an orthopaedic device for repairing and regenerating cartilage. The device includes a plug configured to be positioned in a hole formed in the cartilage and an anchor configured to support the plug and engage the subchondral bone. One or both of the plug and the anchor may be formed from naturally occurring extracellular matrix.

For example, a mass of naturally occurring ECM may be cured to be very rigid and hardened so that it can be machined using conventional cutting tools and/or laser machining. As such, the anchor and/or the plug may be formed by machining a mass of cured matrix to define the structural features thereof. The mass may be formed by compressing the ECM into a solid mass. For example, the ECM may be comminuted and formed into a solid mass with interlocking strands of ECM.

For example, a tightly balled up or compacted mass of pieces of SIS or even comminuted SIS may be hardened by air drying or by hot air drying to become extremely hard. Unexpectedly, this hardened SIS may be machined or formed to have very sharp pointed ends, sharp barbs, etc. With this process, anchors, tacks, barbed tacks, and staples may be machined from such cured mass of SIS.

In one embodiment, there is provided a device for repairing a diseased or damaged portion of articular cartilage on a bone of a joint. The cartilage is prepared by forming an opening therein to remove the diseased or damaged portion. The device includes a plug configured to be positioned in the cartilage opening. The plug has generally the shape of the opening. The device also includes an anchor configured to position and hold the plug in the opening. The plug is formed of naturally occurring extracellular matrix shaped and dried to have a structural strength sufficient to withstand the compression and shear stresses involved in the joint. The plug is secured to the anchor so as to be in contact with the bone.

In regard to another embodiment, there is provided a method for repairing a diseased or damaged portion of articular cartilage on a bone. The method includes the step of forming an opening in the articular cartilage so as to remove the diseased or damaged portion thereof. The method also includes the step of positioning a plug in the opening so as to be adjacent healthy articular cartilage. The plug is formed of a naturally occurring extracellular matrix cured to have a structural rigidity to withstand the compression and shear stress placed on the articular cartilage.

BRIEF DESCRIPTION OF THE DRAWINGS

FIG. 5 is a cross sectional view of a cartilage repair device which utilizes an alternative embodiment of an anchor;

FIG. 6 is a cross sectional view of a cartilage repair device which utilizes an anchor in the form of a staple to secure the assembly to the subchondral bone, note that FIG. 6 includes an encircled portion showing a perspective view of the staple and plug;

DETAILED DESCRIPTION OF THE DRAWINGS

Figure 1:
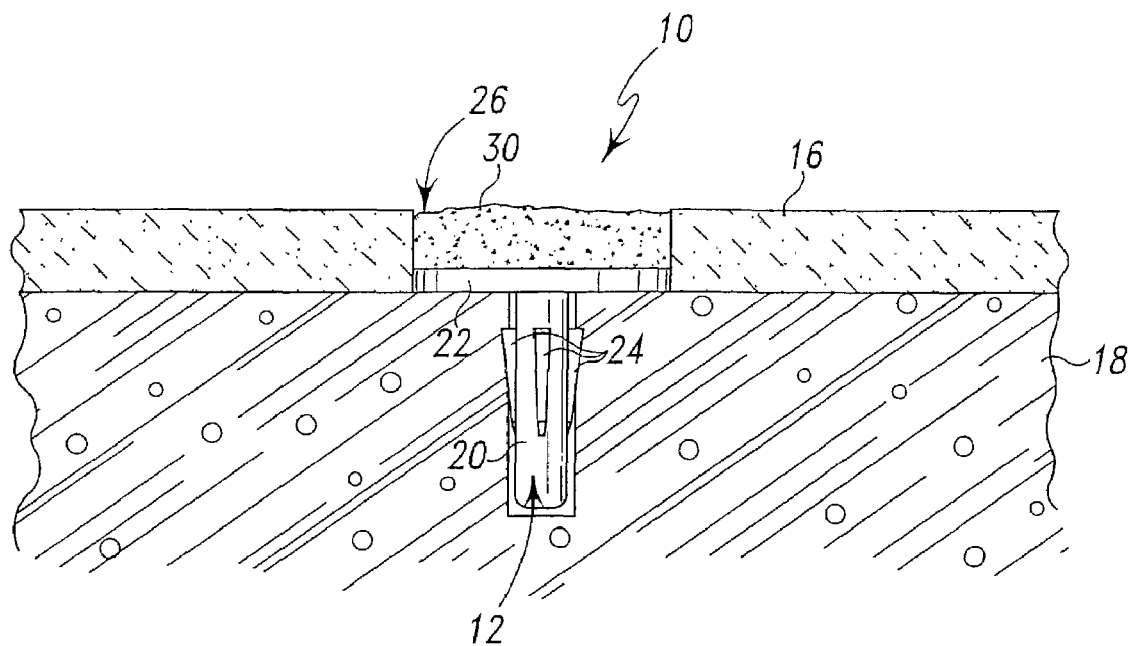
FIG. 1 is a cross sectional view of a cartilage repair device implanted in subchondral bone, note that the anchor is shown in elevation rather than cross section for clarity of description.

While the concepts of the present disclosure are susceptible to various modifications and alternative forms, specific embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives falling within the spirit and scope of the disclosure as defined by the appended claims.

Referring now to FIG. 1, there is shown a cartilage repair device 10 for repairing damaged or diseased cartilage. The device 10 includes an anchor 12 which is anchored or otherwise positioned in an opening formed in both a section of native cartilage 16 and the underlying subchondral bone 18. The anchor 12 is configured to be secured in an area from which damaged, diseased, or destroyed native cartilage and possibly bone have been removed. The anchor 12 includes an elongated central body portion 20 and a head portion 22. The body portion 20 extends downwardly from a lower surface of the head portion 22. As shown in FIG. 1, the body portion 20 may have a number of barbs 24 extending therefrom for engaging the sidewalls of the opening formed in the bone 18. In the illustrative embodiment described herein, the barbs 24 extend radially outwardly and are inclined slightly toward the head portion 22 of the anchor 12.

The cartilage repair device 10 also includes a scaffold or plug 26. The plug 26 is secured to the anchor 12. Specifically, the plug 26 is secured to the upper surface of the head portion 22 of the anchor 12. The plug 26 allows for communication across the removed portion (i.e., the portion of the native cartilage 16 from which the damaged or diseased cartilage has been removed) and the adjacent healthy cartilage. As such, the plug 26 functions as a chondrogenic growth-supporting matrix for promoting a positive cellular response in an effort to achieve articular cartilage regeneration.

The anchor 12 of the cartilage repair device 10 may be constructed of numerous types of synthetic or naturally occurring materials. For example, the anchor 12 may be constructed with a bioabsorbable polymer. Examples of such polymers include: polyesters of [alpha]-hydroxycarboxylic acids, such as poly(L-lactide) (PLLA), polyglycolide (PGA); poly-p-dioxanone (PDO); polycaprolactone (PCL); and any other bioresorbable and biocompatible polymer, co-polymer or mixture of polymers or co-polymers that are commonly utilized in the construction of prosthetic implants. Moreover, the anchor 12 may be constructed with a naturally occurring material such as a naturally occurring ECM (e.g., SIS). In such a case, the head portion 22 and body portion 20 of the anchor 12 may be configured as monolithic structures formed from naturally occurring ECM which is cured to be rigid and hardened to facilitate attachment to the bone 18. As such, it should be appreciated that the ECM material from which the anchor 12 is fabricated is cured to produce a structure which possesses the necessary hardness and toughness to allow the anchor 12 to be driven into bone tissue (i.e., the subchondral bone 18).

It should be understood that the material selected for the anchor 12 may also comprise mixtures or composites of materials. For example, the anchor 12 could comprise both a polymer and ECM material.

ECM material with the necessary hardness and toughness for use as the anchor 12, along with other devices constructed from ECM disclosed herein, may be fabricated by compacting comminuted or shredded naturally occurring ECM material into bar or rod stock by compressing the material together and then curing the material such that it is very rigid and hardened. The curing may be accomplished by simple air drying or by heated air drying of the formed stock. Moreover, the entire structure may be cross-linked.

In a specific exemplary embodiment, the anchor 12 may be constructed with a cured and hardened SIS. In this case, comminuted SIS material is placed in a container and allowed to air dry for a predetermined period of time (e.g., as long as several days) at room temperature. Over such a time, water evaporates from the SIS material thereby shrinking the material. The shrunk material is very tough and hard and, as a result, may be machined as described herein.

It should be appreciated that other process parameters may be established to facilitate the curing process. For example, a curing profile utilizing predetermined amounts of heat and/or pressure may be designed to facilitate the curing of the naturally occurring ECM material (e.g., SIS).

Once the ECM material (e.g., SIS) is cured to a desired hardness and toughness, it may be machined with conventional machining equipment to desired shapes. For example, the anchor 12 may be turned on a lathe or similar equipment to produce the desired configuration of the head portion 22 and the body portion 20 (including, for example, the barbs 24). However, based on the specific design of the anchor 12, it should be appreciated that certain features of the anchor 12 (e.g., the barbs 24) may be separately or additionally machined to produce a desired shape or geometry. For example, various barb configurations may be formed on the body portion 20 of the anchor 12 by, for example, use of a cutting machine.

In addition to conventional machining techniques (e.g., lathing and cutting), contemporary techniques may also be utilized to form the cured naturally occurring ECM into the desired configuration of the anchor 12. For example, a programmable laser cutting machine may be utilized to cut the raw stock of cured ECM. Specifically, the laser cutting machine may be programmed to cut the raw stock in a pattern which produces a desired configuration of the anchor 12. In addition to providing for cutting with precision tolerances, laser cutting also provides other benefits. For example, such laser cutting of the ECM products, for example, barbs having cut edges which are sealed and fused together to enhance the attachment capability of the barbs. In addition, naturally occurring ECM can be molded and cured into the desired shapes.

As alluded to above, the plug 26 functions as a chondrogenic growth-supporting matrix for promoting vascular invasion and cellular proliferation in an effort to achieve articular cartilage regeneration. A central body 30 of the plug 26 is configured as a porous structure constructed from a naturally occurring ECM material such as SIS. As such, when anchored to a defective area of cartilage, cells can migrate into and proliferate within the plug 26, biodegrade the plug 26 while, at the same time, synthesize new and healthy tissue to heal the defective area. The plug 26 may be made out of comminuted and/or lyophilized naturally occurring ECM (e.g. SIS) with the desired porosity and material density. Specifically, the material density and/or porosity of the plug 26 may be varied to control cell migration and proliferation. The cells can migrate from adjacent tissue or from synovial fluid.

The plug 26 may additionally be chemically crosslinked with, for example, aldehydes, carbodiimides, enzymes, or the like. The plug 26 may also be physically crosslinked. Physical crosslinking may be accomplished by freeze-drying or fusing by physical means (e.g., thermal crosslinking by the application of heat, radiation crosslinking by the application of ultraviolet or gamma irradiation, or dehydrothermal crosslinking by the application of a combination of heat and drying).

The plug 26 may also include bioactive agents, biologically derived substances (e.g. stimulants), cells, biologically compatible inorganic materials and/or biocompatible polymers.

"Bioactive agents" include one or more of the following: chemotactic agents; therapeutic agents (e.g. antibiotics, steroidal and non-steroidal analgesics and anti-inflammatories, anti-rejection agents such as immunosuppressants and anti-cancer drugs); various proteins (e.g. short chain peptides, bone morphogenic proteins, glycoprotein and lipoprotein); cell attachment mediators; biologically active ligands; integrin binding sequence; ligands; various growth and/or differentiation agents (e.g. epidermal growth factor, IGF-I, IGF-II, TGF-β I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; TGF$_β$ superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. If other such substances have therapeutic value in the orthopaedic field, it is anticipated that at least some of these substances will have use in concepts of the present disclosure, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft and xenograft), including, for example, meniscal tissue, and derivatives; ligament (autograft, allograft and xenograft) and derivatives; derivatives of intestinal tissue (autograft, allograft and xenograft), including for example submucosa; derivatives of stomach tissue (autograft, allograft and xenograft), including for example submucosa; derivatives of bladder tissue (autograft, allograft and xenograft), including for example submucosa; derivatives of alimentary tissue (autograft, allograft and xenograft), including for example submucosa; derivatives of respiratory tissue (autograft, allograft and xenograft), including for example submucosa; derivatives of genital tissue (autograft, allograft and xenograft), including for example submucosa; derivatives of liver tissue (autograft, allograft and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the concepts of the present disclosure, and such substances should be included in the meaning of "biologically-derived agent" and "biologically-derived agents" unless expressly limited otherwise.

"Biologically derived agents" also include bioremodelable collageneous tissue matrices. The expressions "bioremodelable collagenous tissue matrix" and "naturally occurring bioremodelable collageneous tissue matrix" include matrices derived from native tissue selected from the group consisting of skin, artery, vein, pericardium, heart valve, dura mater, ligament, bone, cartilage, bladder, liver, stomach, fascia and intestine, tendon, whatever the source. Although "naturally occurring bioremodelable collageneous tissue matrix" is intended to refer to matrix material that has been cleaned, processed, sterilized, and optionally crosslinked, it is not within the definition of a naturally occurring bioremodelable collageneous tissue matrix to purify the natural fibers and reform a matrix material from purified natural fibers. The term "bioremodelable collageneous tissue matrices" includes "extracellular matrices" within its definition.

"Cells" include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the concepts of the present disclosure, and such cells should be included within the meaning of "cell" and "cells" unless expressly limited otherwise.

"Biological lubricants" include: hyaluronic acid and its salts, such as sodium hyaluronate; glycosaminoglycans such as dermatan sulfate, heparan sulfate, chondroiton sulfate and keratan sulfate; synovial fluid and components of synovial fluid, including as mucinous glycoproteins (e.g. lubricin), vitronectin, tribonectins, articular cartilage superficial zone proteins, surface-active phospholipids, lubricating glycoproteins I, II; and rooster comb hyaluronate. "Biological lubricant" is also intended to include commercial products such as ARTHREASETM™ high molecular weight sodium hyaluronate, available in Europe from DePuy International, Ltd. of Leeds, England, and manufactured by Bio-Technology General (Israel) Ltd., of Rehovot, Israel; SYNVISC® Hylan G-F 20, manufactured by Biomatrix, Inc., of Ridgefield, N.J. and distributed by Wyeth-Ayerst Pharmaceuticals of Philadelphia, Pa.; HYLAGAN® sodium hyaluronate, available from Sanofi-Synthelabo, Inc., of New York, N.Y., manufactured by FIDIA S.p.A., of Padua, Italy; and HEALON® sodium hyaluronate, available from Pharmacia Corporation of Peapack, N.J. in concentrations of 1%, 1.4% and 2.3% (for opthalmologic uses). If other such substances have therapeutic value in the orthopaedic field, it is anticipated that at least some of these substances will have use in the concepts of the present disclosure, and such substances should be included in the meaning of "biological lubricant" and "biological lubricants" unless expressly limited otherwise.

"Biocompatible polymers" is intended to include both synthetic polymers and biopolymers (e.g. collagen). Examples of biocompatible polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, co-polymer or mixture of polymers or co-polymers that are utilized in the construction of prosthetic implants. In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

"Biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphate, ceramic particles, and combinations of such materials. If other such substances have therapeutic value in the orthopaedic field, it is anticipated that at least some of these substances will have use in the concepts of the present disclosure, and such substances should be included in the meaning of "biocompatible inorganic material" and "biocompatible inorganic materials" unless expressly limited otherwise.

It is expected that various combinations of bioactive agents, biologically derived agents, cells, biological lubricants, biocompatible inorganic materials, biocompatible polymers can be used with the devices of the present disclosure.

Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential aminoacids, glucose, ascorbic acid, sodium pyrovate, fungicides, antibiotics, etc., in concentrations deemed appropriate for cell type, shipping conditions, etc.

It should be understood that the material selected for the plug 26 may also comprise mixtures or composites of materials. For example, the plug 26 could comprise both a polymer and ECM material.

The ECM from which the plug 26 is constructed may be confirmed to have a structural rigidity sufficient to withstand the compression and shear stress to which the cartilage 16 is subjected. Specifically, the plug 26 in the illustrated embodiments has an outer surface which defines an articular surface on which the cartilage from the other bone of the joint bears. As such, the ECM from which the plug 26 is constructed to have the structural rigidity necessary to bear the forces associated with the other bone.

One particularly useful material for fabricating the plug 26 is a porous scaffold or "foam" composed of naturally occurring ECM. For example, the plug 26 may be constructed from a porous SIS foam. In such a manner, both the material density and the pore size of the foam plug 26 may be varied to fit the needs of a given plug design. Such foams may be fabricated by lyophilizing (i.e., freeze-drying) comminuted ECM (i.e., SIS) suspended in water. The material density and pore size of the resultant foam may be varied by controlling, amongst other things, the rate of freezing of the comminuted SIS suspension and/or the amount of water or moisture content in the comminuted SIS at the on-set of the freezing process.

The following is a specific example of a process for fabricating an exemplary SIS foam. The first step in developing a foam with a desired pore size and density is the procurement of comminuted SIS. To do so, scissor-cut SIS runners (~6" long) are positioned in a 1700 series Comitrol™ machine which is commercially available from Urschel Laboratories of Valpraiso, Ind. The SIS material is processed and thereafter collected in a receptacle at the output of the machine. The material is then processed through the machine a second time under similar conditions. The resultant material is a "slurry" of SIS material (thin, long SIS fibers ~200 microns thick×1-5 mm long) suspended substantially uniformly in water.

Thereafter, the comminuted SIS suspension is dried. To do so, a lyophilization process (freeze drying) is used. In particular, the SIS suspension is frozen at a controlled temperature drop rate to control the size of the formed ice crystals. Without allowing the material to thaw, the process of lyopihlization sublimes ice crystals directly to vapor under vacuum and low temperatures. This leaves voids in the spaces previously occupied by ice crystals. One exemplary machine for performing such is a freeze drying process is a Virtis Genesis™ Series lyophilizer which is commercially available from SP Industries, Inc. of Gardiner, N.Y.

The process parameters of the lyophilization process may be varied to produce foams of varying pore sizes and material densities. For example, to produce foams having a relatively large pore size and a relatively low material density, the comminuted SIS suspension may be frozen at a slow, controlled rate (e.g., −1° C./min or less) to a temperature of about −20° C. prior to lyophilization. To produce foams having a relatively small pore size and a relatively high material density, the comminuted SIS may be tightly compacted by removing the water in a substantially uniform manner so as to achieve a relatively high density. Thereafter, the comminuted SIS is flash-frozen using liquid nitrogen prior to lyophilization of the SIS. To produce foams having a moderate pore size and a moderate material density, the comminuted SIS is first tightly compacted by removing the water in a substantially uniform manner so as to achieve a relatively high density. Thereafter, the SIS is frozen at a relatively fast rate (e.g., >−1° C./min) to a temperature of about 80° C. prior to lyophilization of the SIS.

Additional techniques for forming such SIS foams in varying pore sizes and material densities are further described in copending U.S. patent application Ser. No. 10/195,354 entitled "Porous Extracellular Matrix Scaffold and Method", the disclosure of which is hereby incorporated by reference.

In any case, once the plug 26 is fabricated, it is secured to the anchor 12. To do so, the plug 26 may be secured to the anchor 12 in a number of different manners. For example, the plug 26 may be secured to the anchor 12 by virtue of the lyophilization process. Alternatively, the plug 26 may be mechanically secured to the anchor 12 such as by the use of sutures or an adhesive. The plug 26 could also be captured between parts of the anchor 12. Crosslinking could also be used to secure the plug to the anchor.

Figure 2:
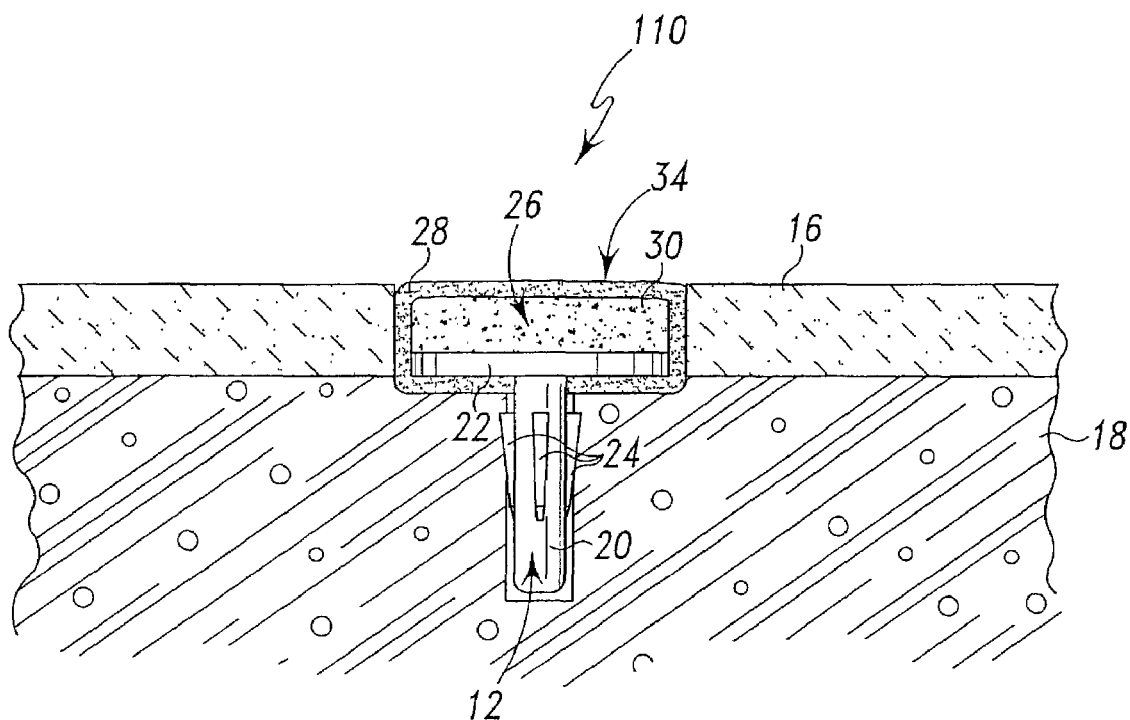
FIGS. 2-4 are views similar to FIG. 1, but showing additional embodiments of a cartilage repair device.

Referring now to FIG. 2, there is shown another embodiment of a cartilage repair device (hereinafter referred to with reference numeral 110). The cartilage repair device 110 is somewhat similar to the cartilage repair device 10. As such, the same reference numerals are utilized in FIG. 2 to identify components which have previously been discussed, with additional discussion thereof being unwarranted. In addition to the anchor 12 and the plug 26, the cartilage repair device 110 includes a cover 34. The cover 34 may assume many different configurations, one of which being a number of sheets 28. The cover 34 is configured to have the structural integrity necessary to bear the forces associated with articulation with the other bone.

The cover 34 (e.g., the sheets 28) may also be utilized to secure the plug 26 to the anchor 12. In particular, as shown in FIG. 2, the sheets 28 may be wrapped around the plug 26 and the head portion 22 of the anchor 12.

The cover 34 (e.g., the sheets 28) may be constructed of the same or different ECM material as the plug 26 (e.g., SIS) and may be perforated to allow easy chemical and cellular transfer. The cover 34 could also be made of a synthetic biocompatible polymer. The cover 34 (e.g., the sheets 28) may be attached to the anchor 12 either by virtue of the lyophilization process or may be mechanically secured to the anchor 12 such as by the use of sutures or an adhesive. The cover 34 may also be chemically or physically crosslinked in a similar manner to as described above in regard to the plug 26. Moreover, bioactive agents, biologically derived substances (e.g. stimulants), cells, biological lubricants, and/or biocompatible inorganic materials as defined above, may be added to the sheets 28.

To produce the desired structural rigidity, the naturally occurring ECM material from which the cover 34 (e.g., the sheets 28) is constructed may be fabricated in a manner similar to as described above in regard to the anchor 12 or the plug 26. Alternatively, the cover 34 may comprise layers 28 of material like the commercially available RESTORE product available from DePuy Orthopaedics of Warsaw, Ind. that have been hardened. The cover 34 may also comprise a mixture or composite of materials. For example, the cover 34 could comprise layers of both polymer and ECM material.

In an exemplary example of the embodiment of FIG. 2, the anchor 12 may be constructed of PLLA, the plug 26 made of a cross-linked SIS foam material, and the cover 34 made of layers of SIS material like the commercially available RESTORE product that has been hardened. The cover 34 can also comprise an element shaped like the upper component 82 of the scaffold fixation device illustrated in FIGS. 7-9 and 11-13 of U.S. Pat. No. 6,371,958 B1, the complete disclosure of which is incorporated by reference herein.

Figure 3:
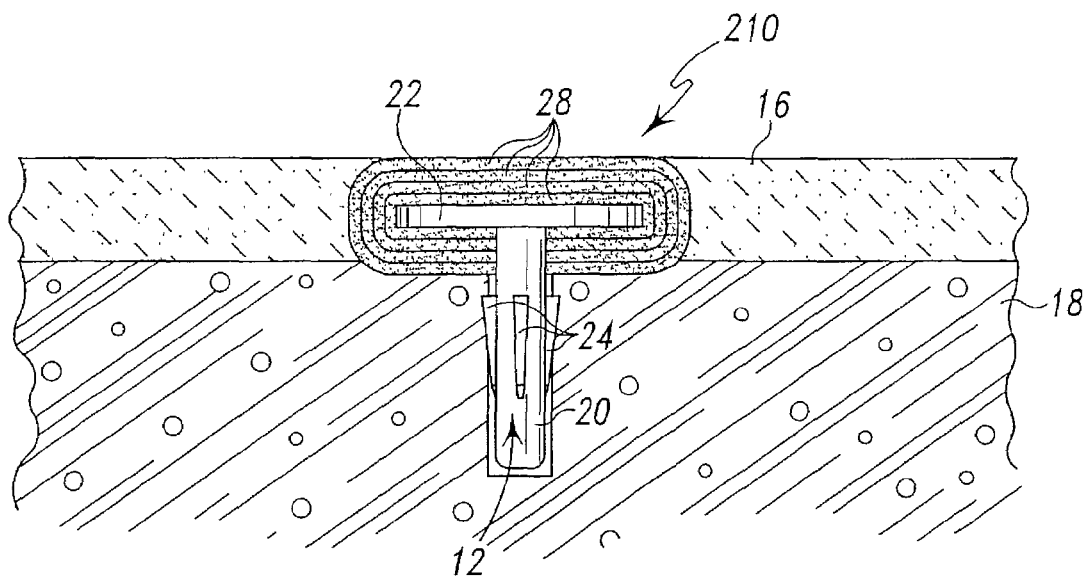

Referring now to FIG. 3, there is shown another embodiment of a cartilage repair device (hereinafter referred to with reference numeral 210). The cartilage repair device 210 is somewhat similar to the cartilage repair devices 10 and 110. As such, the same reference numerals are utilized in FIG. 3 to identify components which have previously been discussed, with additional discussion thereof being unwarranted. The cartilage repair device 210 utilizes a number of the ECM sheets 28 as a chondrogenic growth supporting matrix. As such, the sheets 28 of ECM material function as a "plug" in a similar manner as the plug 26. As shown in FIG. 3, the sheets 28 are secured to the anchor 12 by wrapping the sheets 28 around the head portion 22 of the anchor 12.

Similarly to as described above, the sheets 28 of ECM material of the cartilage repair device 210 may be perforated to allow easy chemical and cellular transfer. In addition to wrapping, the sheets 28 may be further secured to the anchor 12 either by virtue of the lyophilization process or may be mechanically secured to the anchor 12 such as by the use of sutures or an adhesive. The sheets 28 may also be chemically crosslinked. Moreover, bioactive agents, biologically derived substances (e.g. stimulants), biological lubricants, cells, and/or biocompatible inorganic materials as defined above may be added to the sheets 28.

Figure 4:
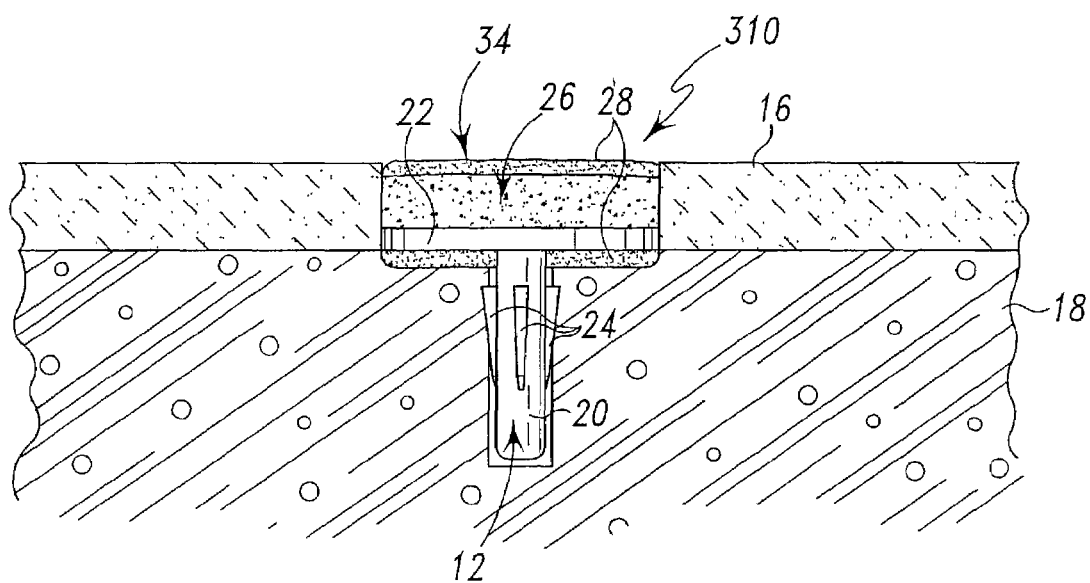

Referring now to FIG. 4, there is shown another embodiment of a cartilage repair device (hereinafter referred to with reference numeral 310). The cartilage repair device 310 is somewhat similar to the cartilage repair devices 10, 110, and 210. As such, the same reference numerals are utilized in FIG. 4 to identify components which have previously been discussed, with additional discussion thereof being unwarranted. The cartilage repair device 310 is essentially the same as the cartilage repair device 110 of FIG. 2, except for the configuration of the cover 34. In particular, the cover 34 (in this case, the sheets 28 of naturally occurring ECM material) does not wrap around the edges of the plug 26 (as does the cover 34 of FIG. 2). In such a configuration, the porous plug 26 is, in effect, sandwiched between a top cover and a bottom cover. The sheets 28 of the cartilage repair device 310, which in this exemplary embodiment function as the cover 34, may be constructed of the same or different ECM material as the plug 26 (e.g., SIS) and may be perforated to allow easy chemical and cellular transfer. The sheets 28 may be attached to the anchor 12 and/or the plug 26 either by virtue of the lyophilization process or may be mechanically secured to the anchor 12 and/or the plug 26 such as by the use of sutures or an adhesive. As described above, the cover 34 (e.g., the sheets 28) of the cartilage repair device 310 may also be chemically crosslinked. Moreover, bioactive agents, biologically derived substances (e.g. stimulants), cells, biological lubricants, biocompatible polymers and/or biocompatible inorganic materials as defined above may be added to the cover 34. Yet further, the cover 34 of the cartilage repair device 310 may also be cured or otherwise fabricated to produce a structure with a desired structural rigidity.

Referring now to FIG. 5, there is shown another embodiment of a cartilage repair device (hereinafter referred to with reference numeral 410). The cartilage repair device 410 is somewhat similar to the cartilage repair devices 10, 110, 210, and 310. As such, the same reference numerals are utilized in FIG. 5 to identify components which have previously been discussed, with additional discussion thereof being unwarranted. The cartilage repair device 410 includes an anchor 412 which is utilized in lieu of the anchor 12 described in regard to FIGS. 1-4. In particular, in the embodiment shown in FIG. 5, the plug 26 is positioned in an osteochondral defect 414 without the use a bottom-mounted anchor (i.e., the anchor 12 of FIGS. 1-4). Similarly to as described above, the plug 26 is constructed out of comminuted and lyophilized naturally occurring ECM (e.g., SIS) having a desired porosity and material density.

The plug 26 is retained in the hole formed in the cartilage 16 and protected from in vivo forces by an annular shaped anchor 412. The anchor 412 may be provided in many different configurations which allow it to be press fit or otherwise anchored into the subchondral bone 18. For example, as shown in FIG. 5, the anchor 412 may be "bottle cap"-shaped so as to allow the anchor 412 to be press fit or otherwise secured into an annular groove 416 formed in the subchondral bone 18. The groove may be formed and the anchor may be shaped as described and shown in Patent Cooperation Treaty publication WO 01/39694 A2, published Jun. 7, 2001 entitled "Fixation Technology", the complete disclosure of which is incorporated by reference herein. Alternatively, the anchor 412 may be mechanically secured to the subchondral bone 18 by use of adhesive or other types of anchoring structures (e.g., barbs).

The anchor 412 of the cartilage repair device 410 may be constructed from numerous types of synthetic or naturally occurring materials. For example, the anchor 12 may be constructed with a bioabsorbable polymer such as PLLA, PGA, PDO, PCL, or any other such bioabsorbable polymer which is commonly utilized in the construction of prosthetic implants. Moreover, the anchor 412 may be constructed from a naturally occurring material such as a naturally occurring ECM (e.g., SIS) which is cured or otherwise fabricated to be rigid and hardened to facilitate attachment to the bone in the same manner as described above in regard to the anchor 12 and/or the plug 26 of FIGS. 1-4.

In the case of when the anchor 412 is constructed from ECM, one or more laminated or non-laminated sheets 28 of the same or different ECM may be utilized. The sheets 28 may surround the plug 26 on three sides, or perhaps all four sides. Alternatively, the anchor may be constructed from formed (e.g., dried and machined) comminuted ECM material. In either configuration, the ECM material may be perforated and may be cured in a similar manner to as described above in regard to the anchor 12 or the plug 26. As with the ECM material previously described above, the ECM material from which the anchor 412 is constructed may also be chemically crosslinked. Moreover, bioactive agents, biologically derived substances (e.g. stimulants), cells, biocompatible polymers, biocompatible inorganic materials, and/or biological lubricants as defined above may be added to the ECM material utilized to construct the anchor 412.

Referring now to FIG. 6, there is shown another embodiment of a cartilage repair device (hereinafter referred to with reference numeral 510). The cartilage repair device 510 is somewhat similar to the cartilage repair devices 10, 110, 210, 310, and 410. As such, the same reference numerals are utilized in FIG. 6 to identify components which have previously been discussed, with additional discussion thereof being unwarranted.

The cartilage repair device 510 includes an anchor 512 which is somewhat similar to the anchor 412 described in regard to FIG. 5. In particular, in the embodiment shown in FIG. 6, the plug 26 is positioned in the hole formed in the cartilage 16 without the use a bottom-mounted anchor (i.e., the anchor 12 of FIGS. 1-4). However, in the case of the cartilage repair device 510 of FIG. 6, the anchor 512 is configured as a staple 520 which secures the plug within the defect 514.

Similarly to as described above, in this embodiment, the plug 26 may be constructed from comminuted and lyophilized naturally occurring ECM (e.g., SIS) having a desired porosity and material density. As shown in FIG. 6, the plug 26 may be wrapped in a cover 34 such as a number of sheets 28 of the same or different ECM which surround the plug 26. It should be appreciated that in a similar manner to the cartilage repair device 210 of FIG. 3, in lieu of a separate plug 26, the sheets 28 of ECM material themselves may function as a chondrogenic growth supporting matrix.

The wrapped plug 26 (or similar matrix formed from the sheets 28) is retained in the defect 514 by inserting the staple 520 into the subchondral bone 18. Alternatively, the wrapped plug 26 (or similar matrix formed from the sheets 28) may be press fit or adhesively secured in the defect 514. In the case of a press fit plug, one or more grooves may be formed in the sheets 28 to facilitate the press fit process.

The staple 520 of the cartilage repair device 510 may be constructed of numerous types of synthetic or naturally occurring materials. For example, the staple 520 may be constructed from a bioabsorbable polymer such as PLLA, PGA, PDO, PCL, or any other such bioabsorbable polymer which is commonly utilized in the construction of prosthetic implants. Moreover, the staple 520 may be constructed from a naturally occurring material such as a naturally occurring ECM (e.g., SIS) which is cured to be rigid and hardened to facilitate attachment to the bone in the same manner as described above in regard to the anchor 12 of FIGS. 1-4 and the anchor 412 of FIG. 5.

The staple 520 can comprise a commercially available product, such as a staple available from the MITEK® Products division of ETHICON, INC. of Westwood, Mass. Moreover, the staple 520 may be embodied as any of the staples or other devices and methods disclosed in U.S. Pat. No. 6,179,840 issued Jan. 30, 2001; U.S. Pat. No. 6,364,884 issued Apr. 2, 2002; U.S. patent application Ser. No. 09/535,183 entitled "Graft Fixation Device Combination" which was filed on Mar. 27, 2000; U.S. patent application Ser. No. 09/535,189 entitled "Instrument for Inserting Graft Fixation Device" which was filed on Mar. 27, 2000; U.S. patent application Ser. No. 09/793,036 entitled "Graft Fixation Device Combination" which was filed Feb. 26, 2001; U.S. patent application Ser. No. 09/793,043 entitled "Methods of Securing a Graft Using a Graft Fixation Device" which was filed on Feb. 26, 2001; U.S. patent application Ser. No. 09/793,216 entitled "Instrument for Inserting Graft Fixation Device" which was filed on Feb. 26, 2001; U.S. patent application Ser. No. 09/864,619 entitled "Graft Fixation Device and Method" which was filed on May 24, 2001; U.S. patent application Ser. No. 10/056,534 entitled "Graft Fixation Device Combination" which was filed on Jan. 24, 2002; and U.S. patent application Ser. No. 10/142,399 entitled "Graft Fixation Device Combination" which was filed on May 9, 2002, the disclosures of each of these patents and patent applications being hereby incorporated by reference.

Figure 7:
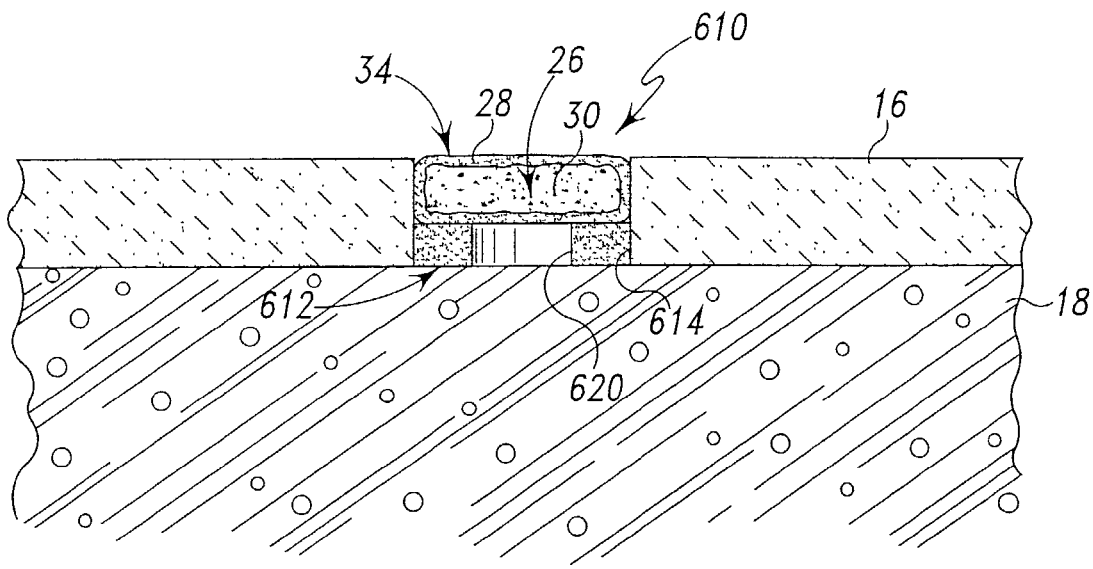
FIG. 7 is a cross sectional view of a cartilage repair device which utilizes an anchor in the form of a ring to secure the assembly to the subchondral bone.

Referring now to FIG. 7, there is shown another embodiment of a cartilage repair device (hereinafter referred to with reference numeral 610). The cartilage repair device 610 is somewhat similar to the cartilage repair devices 10, 110, 210, 310, 410, and 510. As such, the same reference numerals are utilized in FIG. 7 to identify components which have previously been discussed, with additional discussion thereof being unwarranted.

The cartilage repair device 610 includes an anchor 612 which, similarly to the other anchors described herein, is utilized to retain the plug 26 in an osteochondral defect 614. In the embodiment shown in FIG. 7, the anchor 612 is configured as a ring 620 which supports and secures the plug 26 within the defect 614.

Similarly to as described above, the plug 26 utilized in this, or any other embodiment described herein, may be constructed out of comminuted and lyophilized naturally occurring ECM (e.g., SIS) having a desired porosity and material density. As shown in FIG. 7, the plug 26 may be wrapped in a cover 34 such as a number of sheets 28 of the same or different ECM material. It should be appreciated that in a similar manner to the cartilage repair device 210 of FIG. 3, in lieu of a separate plug 26, the sheets 28 of ECM material may themselves function as a chondrogenic growth supporting matrix.

Figure 8:
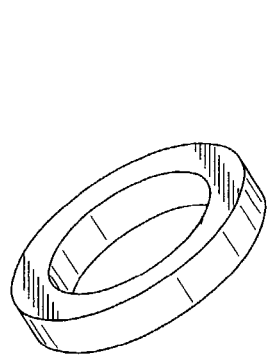
FIGS. 8-10 are perspective views of a number of embodiments of the rings of FIG. 7.
Figure 9:
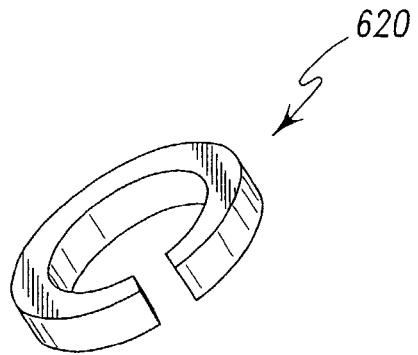
Figure 10:
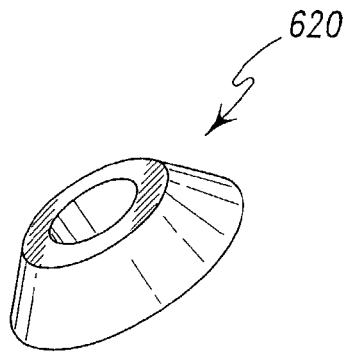

The wrapped plug 26 (or the matrix formed from the sheets 28) is supported and retained in the hole formed in the cartilage 16 by inserting the ring 620 into the hole. As shown in FIGS. 8-10, the ring 620 may be embodied as a closed ring (see FIG. 8), a ring formed with a slot (see FIG. 9), or a ring formed with a taper (see FIG. 10). Such modifications may be utilized to enhance the retention characteristics of the ring 620 in a given application.

The ring 620 of the cartilage repair device 610 may be constructed of numerous types of synthetic or naturally occurring materials. For example, the ring 620 may be constructed with a bioabsorbable polymer such as PLLA, PGA, PDO, PCL, or any other such bioabsorbable polymer which is commonly utilized in the construction of prosthetic implants. Moreover, the ring 620 may be constructed with a naturally occurring material such as a naturally occurring ECM (e.g., SIS) which is cured to be rigid and hardened in the same manner as described above in regard to the anchor 12 of FIGS. 1-4 and the anchors 412 and 512 of FIGS. 5 and 6, respectively. The inner space defined by the ring 620 may be filled with material, such as ECM material (e.g., SIS), subsequent to implantation of the ring 620.

Figure 11:
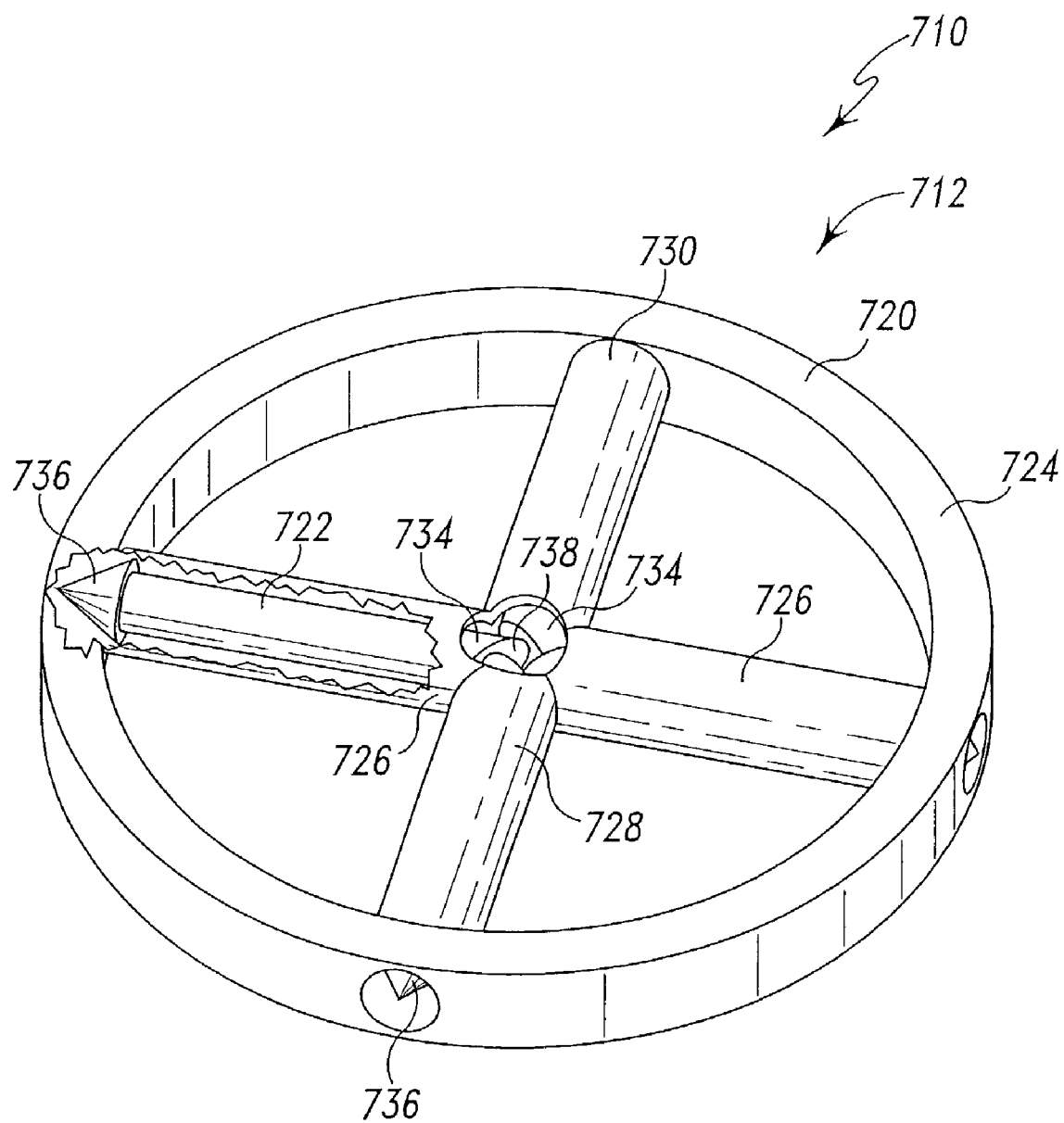
FIG. 11 is an enlarged perspective view of a cartilage repair device which utilizes an alternative embodiment of an anchor, note that a portion of one of the tubes has been cut away for clarity of description to expose the barb positioned therein.
Figure 12:
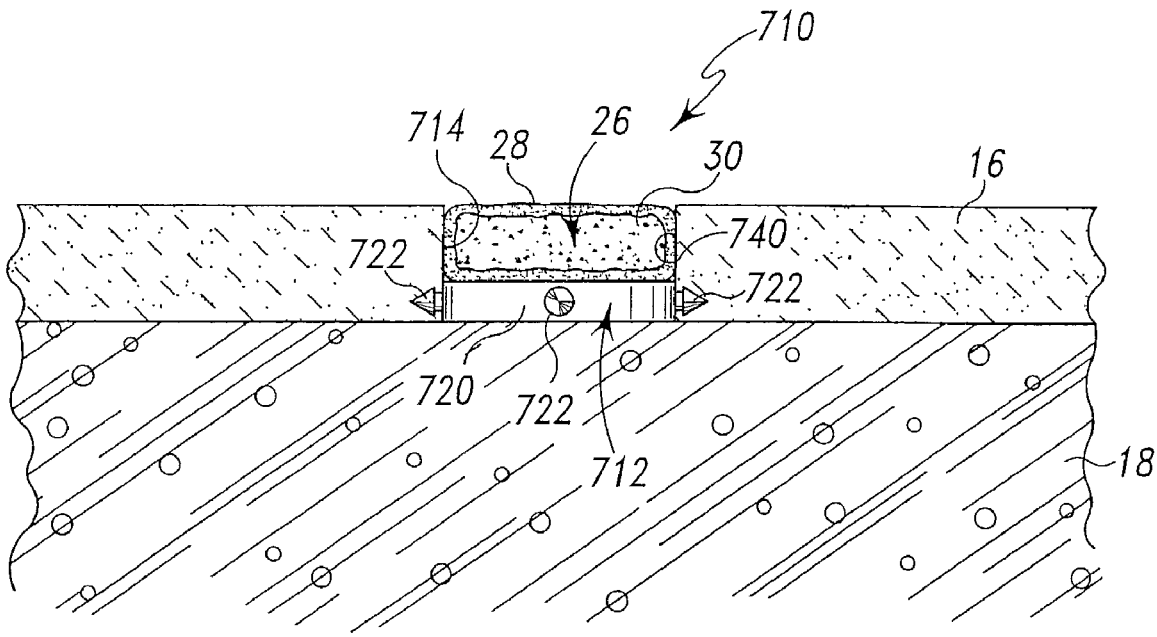
FIG. 12 is a cross sectional view showing the cartilage repair device of FIG. 11 secured to the native cartilage, note that the anchor is shown in elevation rather than cross section for clarity of description.
Figure 13:
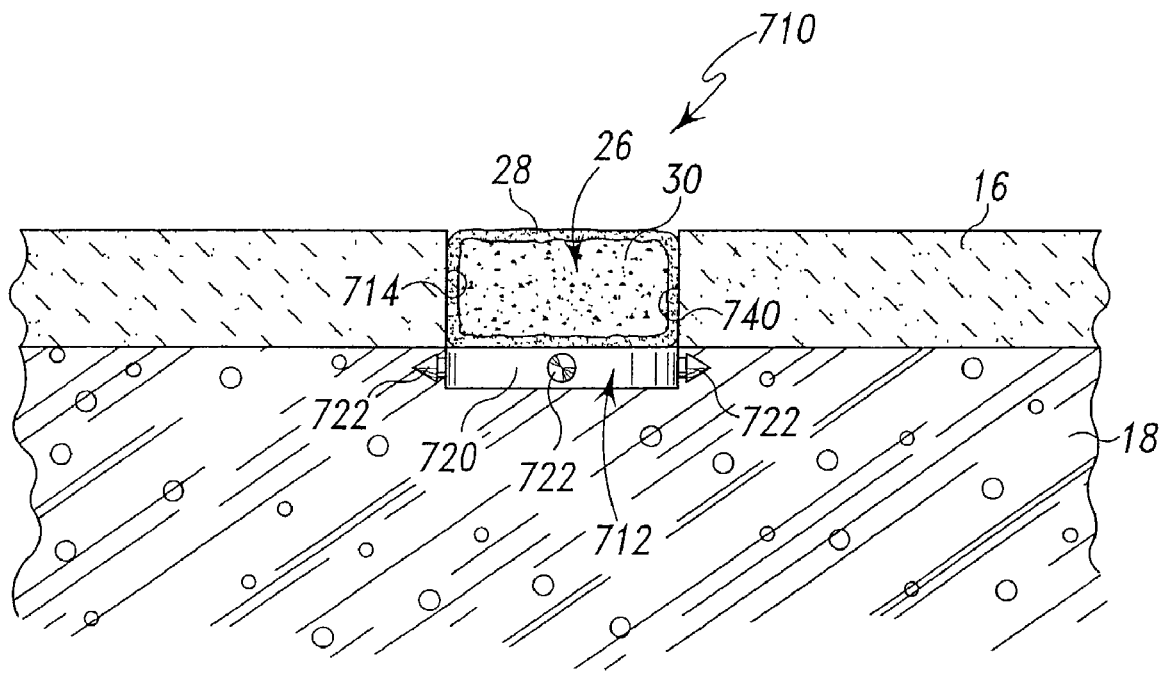
FIG. 13 is a cross sectional view showing the cartilage repair device of FIG. 11 secured to the subchondral bone, note that the anchor is shown in elevation rather than cross section for clarity of description.

Referring now to FIGS. 11-13, there is shown another embodiment of a cartilage repair device (hereinafter referred to with reference numeral 710). The cartilage repair device 710 is somewhat similar to the cartilage repair devices 10, 110, 210, 310, 410, 510, and 610. As such, the same reference numerals are utilized in FIGS. 11-13 to identify components which have previously been discussed, with additional discussion thereof being unwarranted.

The cartilage repair device 710 includes an anchor 712 which, similarly to the other anchors described herein, is utilized to retain the plug 26 in an osteochondral defect 714. In the embodiment shown in FIGS. 11-13, the anchor 712 is configured as a ring 720 which has a number of barbs 722 extending radially outwardly from a center of the ring 720. In particular, the ring 720 includes a ring body 724 and a number of tubes 726. A first end portion 728 of each of the tubes 726 is positioned near the center point of the ring body 724, whereas a second end portion 730 of each of the tubes 726 extends through the ring body 724.

One of the barbs 722 (or other type of engagement member) is positioned in each of the tubes 726. Each of the barbs 722 has a first end 734 which is extendable out of the first end portion 728 of the tube 726, and a second end 736 which is extendable out of the second end portion 730 of the tube 726. The second end 736 of the barbs 722 has a tip, point, or other type of engagement feature defined therein.

Each of the barbs 722 is positionable in either an extended position (as shown in FIGS. 12 and 13) or a retracted position (as shown in FIG. 11). When positioned in its extended position, the pointed end 736 of the barb 722 extends out of the outer end of the tube 726 in which it is positioned (see FIGS. 12 and 13). Conversely, when positioned in its retracted position, the pointed end 736 of the barb 722 is retracted or otherwise received into the outer end of the tube 726 in which it is positioned (see FIG. 11).

The barbs 722 may be selectively moved from their retracted positions to their extended positions subsequent to positioning the ring 720 in the defect. In particular, as shown in FIG. 11, the inner end 734 of the barbs 722 has a cam surface 738 defined therein. In such a way, engagement of the cam surfaces 738 by a complimentary cam surface of an engagement tool (not shown) urges the barbs 722 radially outwardly thereby moving the barbs 722 from their respective retracted positions to their respective extended positions. In an exemplary embodiment, the engagement tool has a spheroid-shaped engagement surface which, upon contact with the cam surfaces 738 of the barbs 722, urges the barbs 722 radially outwardly.

Similarly to as described above, the plug 26 utilized in this, or any other embodiment described herein, may be constructed out of comminuted and lyophilized naturally occurring ECM (e.g., SIS) having a desired porosity and material density. As shown in FIGS. 12 and 13, the plug 26 may be wrapped in a cover 34 such as a number of sheets 28 of the same or different ECM material. It should be appreciated that in a similar manner to the cartilage repair device 210 of FIG. 3, in lieu of a separate plug 26, the sheets 28 of ECM material may themselves function as a chondrogenic growth supporting matrix.

The wrapped plug 26 (or the matrix formed from the sheets 28) is supported and retained in the hole formed in the cartilage 16 by inserting the ring 720 into the hole, and thereafter engaging the sidewall 740 in which the hole is formed with the barbs 722. In particular, once positioned in the hole, the barbs 722 may be urged from their retracted positions to their extended positions thereby causing the pointed ends 736 of the barbs 722 to engage the sidewall 740.

As shown in FIG. 12, the surgical site may be prepared such that the ring 720, when implanted, engages the native cartilage 16. Alternatively, as shown in FIG. 13, the surgical site may be prepared such that the ring 720, when implanted, engages the subchondral bone 18.

The ring 720 of the cartilage repair device 710 may be constructed of numerous types of synthetic or naturally occurring materials. For example, the ring 720 may be constructed with a bioabsorbable polymer such as PLLA, PGA, PDO, PCL, or any other such bioabsorbable polymer which is commonly utilized in the construction of prosthetic implants.

Moreover, the ring 720 may be constructed with a naturally occurring material such as a naturally occurring ECM (e.g., SIS) which is cured to be rigid and hardened in the same manner as described above in regard to the anchor 12 of FIGS. 1-4 and the anchors 412 and 512 of FIGS. 5 and 6, respectively. The ECM material may be perforated and may be cured in a similar manner to as described above in regard to the anchor 12 or the plug 26. As with the ECM material previously described above, the ECM material from which the ring 720 is constructed may also be chemically crosslinked. Moreover, bioactive agents, biologically derived substances (e.g. stimulants), cells, biocompatible polymers, biocompatible inorganic materials, and/or biological lubricants as defined above may be added to the ECM material utilized to construct the ring 720.

The principles of the present disclosure may also be applied to other types of anchors. For example, cartilage repair units like those disclosed in U.S. Pat. No. 5,769,899 to Schwartz et al., the disclosure of which is incorporated by reference herein, can be made with a plug of naturally occurring extracellular matrix, with or without a cover. In addition, cartilage repair units like those disclosed in U.S. Pat. No. 6,251,143 B1 to Schwartz et al., the disclosure of which is incorporated by reference herein, can be made with an insert of naturally occurring extracellular matrix, with or without a cover. Reference is also made to U.S. Pat. No. 6,371,958 B1, discussed above; the entire scaffold fixation device could be made of naturally occurring extracellular matrix.

Hence, the cartilage repair devices described herein have numerous advantages over heretofore designed devices. In particular, heretofore designed devices use, primarily, synthetic polymeric materials. However, synthetic polymers do not possess the advantages naturally occurring extracellular matrices (ECMs), like SIS, which can inherently stimulate cells to proliferate and to synthesize new tissue. However, one or both of the plug and the anchor of the cartilage repair devices described herein may be constructed out of a naturally occurring ECM material such as SIS. Such a device provides an enhanced structure into which cells migrate, proliferate, and synthesize new tissue. Moreover, such a device also possess sufficient mechanical strength and degradation kinetics to successfully withstand in vivo joint forces at least initially following implantation. In addition, for use in combination with devices such as the scaffold fixation device disclosed in U.S. Pat. No. 6,371,958 B1, the plug should possess sufficient mechanical strength and degradation kinetics to successfully withstand the load provided by the anchoring device.

The concepts disclosed in the following copending U.S. Patent Applications, which are incorporated by reference herein, may be combined with the teachings of the present disclosure: Ser. No. 10/195,795 entitled "Meniscus Regeneration Device and Method"; Ser. No. 10/195,719 entitled "Devices from Naturally Occurring Biologically Derived Materials"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; and Ser. No. 10/195,633 entitled "Porous Delivery Scaffold and Method", along with U.S. patent application Ser. No. 10/172,347 entitled "Hybrid Biologic-Synthetic Bioabsorbable Scaffolds" which was filed on Jun. 14, 2002. For example, it may be desirable to use biological lubricants in combination with the concepts of the present disclosure.

For some cartilage repair applications, a repair may be made with a RESTORE™ wafer from DePuy Orthopaedics, Inc. which is seeded with cells to encourage the healing process. For example, RESTORE™ wafers may be seeded with cells supplied by Verigen Transplantation Service International AG (VTSI) in Germany in accordance with processes offered by VTSI. See U.S. Pat. Nos. 6,379,367 and 6,283,980, incorporated by reference herein. Illustratively, a 1.5 cm RESTORE™ wafer, which is typically made by laminating ten layers of SIS together, is supplied to VTSI to be seeded with cells.

Illustratively, therefore, a cartilage implant may comprise a laminate of a plurality of layers of ECM such as SIS, which laminate is seeded with cells such as chondrocyte cells.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the present disclosure arising from the various features of the cartilage repair devices described herein. It will be noted that alternative embodiments of each of the cartilage repair devices of the present disclosure may not include all of the features described yet benefit from at least some of the advantages of such features. Those of ordinary skill in the art may readily devise their own implementations of cartilage repair devices that incorporate one or more of the features of the present disclosure and fall within the spirit and scope of the appended claims.

The invention claimed is:

1. A device for repairing a diseased or damaged portion of articular cartilage on a bone of a joint, the cartilage having been prepared by forming an opening therein to remove the diseased or damaged portion, the device comprising:
a plug configured to be positioned in the opening formed in the cartilage, the plug comprising a shaped and dried naturally occurring extracellular matrix, and
an anchor configured to position and hold the plug in the opening, wherein the anchor is formed of naturally occurring extracellular matrix cured and shaped to fasten into a subchondral portion of the bone.

2. The device of claim 1, wherein the anchor comprises (i) a head portion configured to support the plug and (ii) a body portion extending from the head portion to fasten into the subchondral portion of the bone.

3. The device of claim 2, wherein the body portion has outwardly extending barbs to engage the subchondral portion of the bone.

4. The device of claim 1, wherein the naturally occurring extracellular matrix from which the anchor is formed comprises SIS.

5. The device of claim 1, wherein the naturally occurring extracellular matrix from which the anchor is formed comprises comminuted SIS.

6. The device of claim 1, wherein the naturally occurring extracellular matrix from which the anchor is formed comprises crosslinked SIS.

7. The device of claim 1, wherein the plug is lyophilized onto the anchor.

8. The device of claim 1, wherein the plug is adhesively attached to the anchor.

9. The device of claim 1, wherein the plug is sutured to the anchor.

10. The device of claim 1, wherein (i) the anchor is formed with a head portion to support the plug and a body portion extending from the head portion to fasten into the subchondral portion of the bone, and (ii) the plug is formed to be sufficiently porous to receive cells from adjacent tissue or from synovial fluid and is lyophilized onto the head portion.

11. A method for repairing a diseased or damaged portion of articular cartilage on a bone, the method comprising the steps of:

forming an opening in the articular cartilage so as to remove the diseased or damaged portion thereof;

positioning a plug in the opening so as to be proximate to healthy articular cartilage, wherein the plug comprises a shaped and dried naturally occurring extracellular matrix;

securing the plug to an anchor;

forming an opening in the subchondral portion of the bone; and wherein (i) the anchor is formed of SIS and (ii) the step of positioning the plug in the opening formed in the cartilage comprises positioning the anchor in the opening formed in the subchondral portion of the bone so as to position the plug in the opening formed in the cartilage.

12. A method of forming a device for repairing a diseased or damaged portion of articular cartilage on a bone, the method comprising the steps of:

providing a plug configured conformingly to fit into an opening formed in the cartilage to remove the diseased or damaged portion, the plug comprising a naturally occurring extracellular matrix having a porosity sufficient to promote cell migration from surrounding healthy tissue and synovial fluid, the plug being biodegradable over time in the cartilage opening and effective to synthesize new and healthy cartilage over such time to close and heal the opening, and providing an anchor configured to position and hold the plug in the opening in contact with the healthy cartilage and subchondral portion of the bone adjacent the opening, wherein the anchor providing step comprises forming a mass of naturally occurring extracellular matrix cured to have sufficient rigidity and strength to position and hold the plug in the opening.

13. A method of forming a device for repairing a diseased or damaged portion of articular cartilage on a bone, the method comprising the steps of:

providing a plug configured conformingly to fit into an opening formed in the cartilage to remove the diseased or damaged portion, the plug comprising a naturally occurring extracellular matrix having a porosity sufficient to promote cell migration from surrounding healthy tissue and synovial fluid, the plug being biodegradable over time in the cartilage opening and effective to synthesize new and healthy cartilage over such time to close and heal the opening, and providing an anchor configured to position and hold the plug in the opening in contact with the healthy cartilage and subchondral portion of the bone adjacent the opening, wherein the anchor providing step comprises forming a mass of SIS cured to have sufficient rigidity and strength to position and hold the plug in the opening.

14. A device for repairing a diseased or damaged portion of articular cartilage on a bone of a joint, the cartilage having been prepared by forming an opening therein to remove the diseased or damaged portion, the device comprising:

a plug configured to be positioned in the opening formed in the cartilage, the plug comprising a shaped naturally occurring extracellular matrix, and an anchor configured to position and hold the plug in the opening, wherein the anchor is formed of naturally occurring extracellular matrix cured and shaped to fasten into a subchondral portion of the bone.

15. The device of claim 14, wherein the anchor comprises (i) a head portion configured to support the plug, and (ii) a body portion extending from the head portion to fasten into the subchondral portion of the bone.

16. The device of claim 15, wherein the body portion has outwardly extending barbs to engage the subchondral portion of the bone.

17. The device of claim 14, wherein the naturally occurring extracellular matrix from which the anchor is formed comprises SIS.

18. The device of claim 14, wherein the naturally occurring extracellular matrix from which the anchor is formed comprises comminuted SIS.

19. The device of claim 14, wherein the naturally occurring extracellular matrix from which the anchor is formed comprises crosslinked SIS.

20. The device of claim 14, wherein the plug is lyophilized onto the anchor.

21. The device of claim 14, wherein the plug is adhesively attached to the anchor.

22. The device of claim 14, wherein the plug is sutured to the anchor.

23. The device of claim 14, wherein (i) the anchor is formed with a head portion to support the plug and a body portion extending from the head portion to fasten into the subchondral portion of the bone, and (ii) the plug is formed to be sufficiently porous to receive cells from adjacent tissue or from synovial fluid.

24. The device of claim 23, wherein the plug is lyophilized onto the head portion.

* * * * *